United States Patent [19]

Gordon

[11] E Patent Number: Re. 33,000

[45] Reissued Date of Patent: Jul. 25, 1989

[54] THERAPEUTIC COMPOSITION AND METHOD OF TREATING VIRUSES

[75] Inventor: Paul Gordon, Chicago, Ill.

[73] Assignee: Greenwich Pharmaceuticals, Incorporated, Greenwich, Conn.

[21] Appl. No.: 474,737

[22] Filed: Mar. 18, 1983

Related U.S. Patent Documents

Reissue of:

[64] Patent No.: 4,017,608
Issued: Apr. 12, 1977
Appl. No.: 609,724
Filed: Sep. 2, 1975

U.S. Applications:

[60] Continuation of Ser. No. 224,443, Jan. 12, 1981, abandoned, which is a continuation of Ser. No. 29,039, Apr. 11, 1979, abandoned, which is a division of Ser. No. 424,786, Dec. 14, 1973, Pat. No. 3,939,146, which is a continuation-in-part of Ser. No. 337,134, Mar. 1, 1973, Pat. No. 3,939,145.

[51] Int. Cl.[4] ..... A61K 31/70; C12P 5/00; C07H 5/06

[52] U.S. Cl. ..... 514/25; 435/1; 514/23; 514/62; 536/4.1; 536/17.2; 536/17.3; 536/18.7; 536/55.2

[58] Field of Search ..... 424/180; 435/72, 1; 514/25

[56] References Cited

U.S. PATENT DOCUMENTS

| | | | |
|---|---|---|---|
| 3,016,372 | 1/1962 | Krimmel | 424/180 |
| 3,723,617 | 3/1973 | Sutton | 424/180 |
| 4,017,608 | 4/1977 | Gordon | 424/180 |

FOREIGN PATENT DOCUMENTS

| | | | |
|---|---|---|---|
| 2505772 | 1/1972 | Japan | 536/4 |

OTHER PUBLICATIONS

Derwent Abstract of Japanese Patent JA 7225057, 1972.

*Primary Examiner*—Johnnie R. Brown
*Attorney, Agent, or Firm*—Finnegan, Henderson, Farabow, Garrett & Dunner

[57] ABSTRACT

The invention provides a novel therapeutic composition comprising a pharmaceutically acceptable carrier containing a therapeutically effective amount of an ethereal monosubstitution of a monosaccharide derivative having the general formula S-O-Y, wherein S is the residue of the monosaccharide derivative selected from the group consisting of pentoses, hexoses and heptoses as single or polysubstituted acetals, ketals or esters and Y is selected from the group consisting of cyclic monovalent nitrogen-containing organic radicals and residua and monovalent organic radicals and residua having the general formula

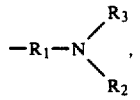

wherein $R_1$ is a divalent organic radical having a linear carbon chain length of about 1–7 carbon atoms and $R_2$ and $R_3$ are selected from the group consisting of —H, —OH, —SH; halogen and monovalent organic radicals and residua having a linear carbon chain length of about 1–7 carbon atoms. The invention also provides certain novel ethereal monosubstitutions of monosaccharide derivatives, of which 3-O-3'-(N',N'-dimethylamino-n-propyl)-1,2-O-isopropylidene-D-glucofuranose is an example. The novel monosaccharide derivatives show striking antiviral activity or other therapeutically valuable properties and are useful as active ingredients in the above therapeutic composition.

The invention further provides a method of therapeutically treating warm-blooded animals with the aforementioned therapeutic composition and novel monosubstituted monosaccharide derivatives.

49 Claims, No Drawings

THERAPEUTIC COMPOSITION AND METHOD OF TREATING VIRUSES

Matter enclosed in heavy brackets [ ] appears in the original patent but forms no part of this reissue specification; matter printed in italics indicates the additions made by reissue.

RELATED APPLICATION

[This] *This application is a continuation, of application Ser. No. 224,443, filed 1/12/81, now abandoned, which is a continuation of Ser. No. 29,039, now abandoned, which is a reissue of Ser. No. 609,124, now U.S. Pat. No. 4,017,608 which* is a division of application Ser. No. 424,786 filed Dec. 14, 1973, and now U.S. Pat. No. 3,939,146, is a continuation in part of application Ser. No. 424,786, in turn, my copending application Ser. No. 337,134, filed on Mar. 1, 1973 and now U.S. Pat. No. 3,939,145, for Therapeutic Composition, Novel Compounds Useful Therein and Method of Using the Same.

BACKGROUND OF THE INVENTION

The present invention is concerned with a novel therapeutic composition and a method of therapeutically treating warm-blooded animals therewith. In one of its more specific variants, the invention further relates to certain novel ethereal monosubstitutions of monosaccharide derivatives which are especially useful as ingredients in the aforementioned composition and in practicing the aforementioned method.

Many diseases caused by certain living microorganisms may be treated very effectively by administering a therapeutically effective amount of an antibiotic. However, antibiotics are not effective in the treatment of virus infections insofar as suppressing the proliferation of the virus particles and reducing cell damage are concerned.

A number of substances other than antibiotics have been proposed heretofore for use in treating virus infections, but they have not been used extensively for a number of reasons. For instance, the previously proposed antiviral agents usually exhibit very low antiviral activity and have little positive effect on the course of the viral infection. The previously proposed antiviral drugs also have not been effective in the treatment of a wide spectrum of virus infections and this has been a major disadvantage. The therapeutic treatment of a large number of patients having undetermined viral infections of widely differing types is impractical with the narrow spectrum prior art antiviral drugs, as it is too difficult to determine the exact virus causing the infection and then select an effective drug. Many potentially effective antiviral drugs are toxic and cannot be safely administered to patients, and still other antiviral drugs have undesirable side effects. As a result of the foregoing and other deficiencies, it is apparent that an entirely satisfactory wide spectrum nontoxic antiviral drug has not been available heretofore for routinely administering to patients having a viral infection caused by many of the common viruses.

It has been discovered that certain ethereal monosubstitutions of monosaccharide derivatives provide important biological signals which allow living cells to resist virus infections. As will be described in greater detail hereinafter, the signals also provide other types of control in cell chemistry.

The therapeutic compositions of the invention overcome the disadvantages of the prior art antiviral agents noted above, and also produce other unusual and unexpected results. For example, the ethereal monosubstitutions of monosaccharide derivatives described hereinafter are therapeutically effective at very low concentrations, while at the same time they exhibit no side effects and are very nontoxic. The ratio of the minimum toxic to therapeutic dose is greater than 50 in both tissue culture and animals.

The antiviral compounds and the therapeutic compositions containing the same disclosed and claimed in my earlier filed copending application Ser. No. 337,134 and now U.S. Pat. No. 3,939,145 possess striking antiviral properties and are highly effective in the treatment of a wide variety of viral infections in warm blooded animals. Nevertheless, the earlier described antiviral compounds and therapeutic compositions do have certain limitations and disadvantages which are over come by the present invention. For example, the earlier described compounds possess strong hydrophilic properties due to the presence of a plurality of free hydroxyl groups which result in several limitations on the effective use thereof in situ including short shelf life, variability of the stability in solution as a function of temperature, and extreme hygroscopicity.

The compounds of the present invention have been found to be more desirable with respect to the properties listed above. This is presently believed to be the direct result of a decrease in the hydrophilic properties and, thereby, an increase in the solubility of the compounds in the fatty tissues of a warm-blooded animal which has been therapeutically treated therewith. This technique also aids in the transportation of the drug to a desired tissue or the concentration thereof on a desired tissue. In the practice of one variant of the invention, an organic substituent is selected which blocks at least one free monosaccharide hydroxyl group and thereby decreases the hydrophilic properties and allows the compound to be transported or concentrated in fatty tissues. In a further variant, a labile organic substituent is selected which may be removed in vivo during treatment of the warm-blooded animal after it has served its purpose, thereby unblocking the hydroxyl group(s).

It is an object of the present invention to provide a therapeutic composition including a pharmaceutically acceptable carrier and a therapeutically effective amount of certain ethereal monosubstitutions of monosaccharide derivatives to be described more fully hereinafter.

It is a further object to provide certain novel compounds to be described more fully hereinafter, which are ethereal monosubstitutions of monosaccharide derivatives exhibiting striking antiviral activity and/or other therapeutically valuable properties.

It is still a further object to provide a therapeutic composition containing one or more of the novel monosaccharide derivatives of the invention.

It is still a further object to provide a method of therapeutically treating a warm-blooded animal wherein the above described therapeutic composition and/or novel monosaccharide derivatives are administered thereto in a therapeutically effective amount.

Still other objects and advantages of the invention will be apparent to those skilled in the art upon reference to the following detailed description.

DETAILED DESCRIPTION OF THE INVENTION INCLUDING PREFERRED VARIANTS THEREOF

The novel therapeutic composition of the invention comprises a pharmaceutically acceptable carrier and a therapeutically effective amount of an ethereal monosubstitution of a monosaccharide derivative having the general formula S-O-Y and organic and inorganic acid salts thereof, wherein S is the residue of a monosaccharide selected from the group consisting of pentoses, hexoses and heptoses which has been derivatized with (a) one or more aliphatic alcohols containing 1-18 carbon atoms and preferably 1-4 carbon atoms to produce an [acetal] *ether* group at one or more available hydroxyl residua, (b) one or more aldehydes containing 1-18 carbon atoms and preferably 1-4 carbon atoms to produce single or multiple acetal groups at one or more available hydroxyl residua, (c) one or more ketones containing 1-18 carbon atoms and preferably 1-4 carbon atoms to produce single or multiple ketal groups at one or more available hydroxyl residua, or (d) one or more organic acid residua containing 1-18 carbon atoms and preferably 1-4 carbon atoms to produce ester groups at one or more available hydroxyl residua, and Y is selected from the group consisting of cyclic monovalent nitrogen-containing organic radicals and residua and monovalent organic radicals and residua having the general formula

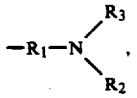

wherein $R_1$ is a divalent organic radical having a [linear] carbon chain length of about 1-7 carbon atoms and $R_2$ and $R_3$ are selected from the group consisting of —H, —OH, —SH, halogen and monovalent organic radicals and residua having a [linear] carbon chain length of about 1-7 carbon atoms. When $R_2$ and $R_3$ is halogen, the halogen may be F, Cl, Br or I, of which Cl or Br is usually preferred. The organic radical $R_1$, and $R_2$ and $R_3$ when they are organic radicals, may be branched or unbranched linear carbon chains and may be saturated or unsaturated, and, when saturated, the linear and/or branched carbon chains may contain one or more double or triple carbon-to-carbon bonds. The linear and/or branched carbon chains of $R_1$, $R_2$ and $R_3$ may be substituted or unsubstituted and, when substituted, one or more substituents may be present, such as —OH, —SH, halogen (F, Cl, Br and/or I), branched or unbranched and saturated or unsaturated hydrocarbon radicals containing 1-7 and preferably 1-3 carbon atoms, —$OR_4$ and/or —$SR_4$ radicals wherein $R_4$ is a branched or unbranched and saturated or unsaturated hydrocarbon radical containing 1-7 and preferably 1-3 carbon atoms, carboxylic acid residua containing 1-7 and preferably 1-3 carbon atoms, and amino groups and aminohydrocarbon radicals containing 1-7 and preferably 1-3 carbon atoms. Preferably $R_1$ is a hydrocarbon radical having a linear carbon chain length of 1-3 or 1-4 carbon atoms and $R_2$ and $R_3$ are individually selected from the group consisting of hydrogen and/or hydrocarbon radicals having linear carbon chain lengths of 1-3 or 1-4 carbon atoms.

Examples of compounds from which cyclic organic radicals and residua are derived include (a) monovalent nitrogen containing saturated, unsaturated or aromatic carbocyclic compounds containing about 4-8 carbon atoms in the ring and preferably about 5-6 carbon atoms in the ring and at least one nitrogen atom attached thereto or to an organo substituent thereon, (b) heterocyclic organic compounds containing about 3-8 carbon atoms in the ring and at least one ring nitrogen atom and (c) derivatives of the foregoing compounds wherein at least one substituent is present, such as —OH, —SH, halogen (F, Cl, Br and/or I), branched or unbranched and saturated or unsaturated hydrocarbon radicals containing 1-7 and preferably 1-3 carbon atoms, —$OR_5$ and/or —$SR_5$ radicals wherein $R_5$ is a branched or unbranched and saturated or unsaturated hydrocarbon radical containing 1-7 and preferably 1-3 carbon atoms, carbocyclic acid residua containing 1-7 and preferably 1-3 carbon atoms, and amino groups and aminohydrocarbon radicals containing 1-7 and preferably 1-3 carbon atoms.

The derivatized monosaccharide residue S may exist in an open chain or cyclic form having the general formulae:

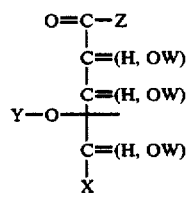

(a)

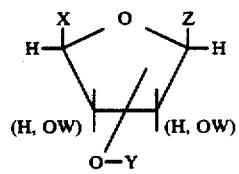

(b)

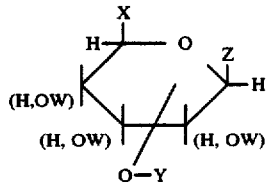

(c)

wherein X and Z are H, OH, hydroxyalkyl, alkoxyl and/or alkoxyalkyl containing up to 3 carbon atoms, W is H, alkyl, alkenyl, cyclic alkane or cyclic aromatic containing 1-18 and preferably 1-6 carbon atoms or acyl containing 1-18 and preferably 1-4 carbon atoms, and Y represents the same organic radicals and residua as aforementioned for the general formula S-O-Y. The above general formulae illustrate the various isomers of the pentoses, hexoses, and heptoses, the relative spatial configuration of the —H and —OH groups about the ring, and the monosubstitution thereof in accordance with one presently preferred variant of the invention. The hydroxyl or alkoxyl residue of the hemiacetal or hemiketal linkage may assume an $\alpha$ or a $\beta$ configuration. The compounds of the invention may be in the form of anomers or mixtures of anomers.

The configurations of the various derivatives of isomers of the pentoses, hexoses and heptoses are well known to those skilled in this art and numerous reference books are available on the subject, the teachings of which are incorporated herein by reference. For example, see Textbook of Biochemistry, 4th Edition, by West et al (1966) and The Monosaccharides by Stanek, Cerny, Kocourek and Pacak (1963). The prior art discloses, for example, a total of eight open chain isomers for the reducing hexoses, and an even larger number of open chain isomers for the reducing heptoses. Either the D-series or the L-series of the pentoses, hexoses and heptoses may be used in practicing the invention, but it is usually preferred to use the D-series. The hexoses often give the best results and especially D-talose, D-galactose, L-galactose, D-idose, D-gulose, D-mannose, D-glucose, L-glucose, D-altrose and D-allose. The aforementioned pentoses, hexoses and heptoses may be ethereally monosubstituted in any available position and derivatized at one or more of the remaining hydroxyl groups. Nevertheless, it is understood that substitution of certain positions of specific monosaccharide derivatives results in more therapeutically active or less toxic compounds. For instance, substitution of the 3-O- position of 1,2-O-isopropylidene-D-glucofuranose or 1,2:5,6-di-O-isopropylidene-D-glucofuranose and the 6-O- position of 1,2-O-isopropylidene-D-galactopyranose or 1,2:3,4-di-O-isopropylidene-D-galactopyranose results in especially valuable compounds.

The following substituents may be ethereally substituted on any of the available positions of the various isomers of the pentoses, hexoses and heptoses to produce nontoxic compounds having exceptional therapeutic activity:

-(n-propylamino),
-(N',N'-dimethylamino-n-propyl),
-(N',N'-dimethylaminoisopropyl),
-(N'-methylpiperidyl),
-(N',N'-dimethylaminoethyl),
-(N',N'-diethylaminoethyl),
-(2',N',N'-trimethylamino-n-propyl),
-dimethylamino,
-(N',N'-dimethylaminomethyl),
-(N',N'-dimethylaminopropyl),
-(N',N'-dimethylamino-iso-butyl),
-(N',N'-dimethylamino-n-butyl),
-(N',N'-dimethylamino-iso-pentyl),
-(N',N'-dimethylaminopentyl),
-(N'-methylamino-n-propyl),
-(N'-methyl-N'-ethylamino-n-propyl),
-(N',N'-diethylamino-n-propyl),
-(amino-n-propyl),
-(N'-ethylamino-n-propyl),
-(N'-propylamino-n-propyl),
-(N',N'-iso-propylamino-n-propyl),
-(1',2'-ethylimino-n-propyl),
-(1''-n-propylpyrrolidyl),
-(1''-n-propylpiperidyl),
-piperidyl,
-(N',N'-dimethylamino-sec-butyl).

Of the foregoing substituents, -(N',N'-dimethylamino-n-propyl) is presently preferred and especially when substituted in the 3-O- position of 1,2-O-isopropylidene-D-glucofuranose or 1,2:5,6-di-O-isopropylidene-D-glucofuranose or the 6-O- position of 1,2-O-isopropylidene-D-galactopyranose or 1,2:3,4-di-O-isopropylidene-D-galactopyranose.

The following compounds have been found to have exceptional wide spectrum antiviral activity and other therapeutically valuable properties and are presently preferred for use in the composition and method of the invention:

3-O-3'-(n-propylamino)-1,2-O-isopropylidene-D-glucofuranose,
3-O-3'-(N',N'-dimethylamino-n-propyl)-1,2-O-isopropylidene-D-glucofuranose,
3-O-4'-(N'-methylpiperidyl)-1,2-O-isopropylidene-D-glucofuranose,
3-O-2'-(N',N'-dimethylaminoethyl)-1,2-O-isopropylidene-D-glucofuranose,
3-O-2'-(N',N'-diethylaminoethyl)-1,2-O-isopropylidene-D-glucofuranose,
3-O-3'-(2',N',N'-trimethylamino-n-propyl)-1,2-O-isopropylidene-D-glucofuranose,
3-O-2'-(N',N'-dimethylaminopropyl)-1,2-O-isopropylidene-D-glucofuranose,
6-O-3'-(N',N'-dimethylamino-n-propyl)-1,2-O-isopropylidene-D-galactopyranose,
6-O-2'-(N',N'-dimethylaminopropyl)-1,2-O-isopropylidene-D-galactopyranose,
3-O-3'-(n-propylamino)-1,2:5,6-di-O-isopropylidene-D-glucofuranose,
3-O-3'-(N',N'-dimethylamino-n-propyl)-1,2:5,6-di-O-isopropylidene-D-glucofuranose,
3-O-4'-(N'-methylpiperidyl)-1,2:5,6-di-O-isopropylidene-D-glucofuranose,
3-O-2'-(N',N'-dimethylaminoethyl)-1,2:5,6-di-O-isopropylidene-D-glucofuranose,
3-O-2'-(N',N'-diethylaminoethyl)-1,2:5,6-di-O-isopropylidene-D-glucofuranose,
3-O-3'-(2',N',N'-trimethylamino-n-propyl)-1,2:5,6-di-O-isopropylidene-D-glucofuranose,
3-O-2'-(N',N'-dimethylaminopropyl)-1,2:5,6-di-O-isopropylidene-D-glucofuranose,
6-O-3'-(N',N'-dimethylamino-n-propyl)-1,2:3,4-di-O-isopropylidene-D-galactopyranose,
6-O-2'-(N',N'-dimethylaminopropyl)-1,2:3,4-di-O-isopropylidene-D-galactopyranose,
α-N',N'-dimethylamino-iso-propyl-2,3:5,6-di-O-isopropylidene-D-glucofuranoside,
and organic and inorganic acid salts thereof.

Of the foregoing compounds, 3-O-3'-(N',N'-dimethylamino-n-propyl)-1,2-O-isopropylidene-D-glucofuranose is presently preferred.

Additional compounds of the general formula S-O-Y, wherein Y is

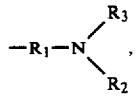

which may be used in practicing the invention are listed below:

| Monosaccharide Residue (S) | Substituent (Y) $R_1$ | $R_2$ | $R_3$ |
|---|---|---|---|
| 3-O—1,2-O—isopropylidene -D-glucofuranose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O—1,2-O—isopropylidene -D-galactopyranose | 3'n-propyl | H | methyl |
| " | " | ethyl | " |

-continued

| Monosaccharide Residue (S) | Substituent (Y) $R_1$ | $R_2$ | $R_3$ |
|---|---|---|---|
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |
| 3-O—1,2:5,6-di-O—iso-propylidene-D-gluco-furanose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O—1,3:3,4-di-O—iso-propylidene-D-galactopyranose | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |

Still other compounds of the general formula S-O-Y, wherein Y is a cyclic monovalent nitrogen-containing organic radical or residue, which may be used in practicing the invention, are as follows:

| Monosaccharide Residue (S) | Substituent (Y) Cycle Radical | Substituent on the Cyclic Radical |
|---|---|---|
| 3-O—1,2-O—isopropylidene-D-glucofuranose | 4'-piperidyl | H |
| " | 3'-piperidyl | methyl, H |
| " | 2'-piperidyl | " |
| " | 3'-pyrrolidyl | " |
| " | 2'-pyrrolidyl | " |
| 6-O—1,2-O—isopropylidene D-galactopyranose | 4'-piperidyl | H |
| " | 3'-piperidyl | methyl, H |
| " | 2'-piperidyl | " |
| " | 3'-pyrrolidyl | " |
| " | 2'-pyrrolidyl | " |
| 3-O—1,2:5,6-di-O—iso-propylidene-D-glucofuranose | 4'-piperidyl | H |
| " | 3'-piperidyl | methyl, H |
| " | 2'-piperidyl | " |
| " | 3'-pyrrolidyl | " |
| " | 2'-pyrrolidyl | 10 methyl, H |
| 6-O—1,2:3,4-di-O—isopropylidene-D-galactopyranose | 4'-piperidyl | H |
| " | 3'-piperidyl | methyl, H |
| " | 2'-piperidyl | " |
| " | 3'-pyrrolidyl | " |
| " | 2'-pyrrolidyl | " |

The present invention also provides certain novel compounds which have wide spectrum antiviral activity. The novel compounds may be defined generically as follows:

3-O-3'-(N',N'-dimethylamino-n-propyl)-1,2-O-isopropylideneglucofuranose,

3-O-4'-(N'-methylpiperidyl)-1,2-O-isopropylideneglucofuranose,

3-O-2'-(N',N'-dimethylaminoethyl)-1,2-O-isopropylideneglucofuranose,

3-O-3'-(2',N',N'-trimethylamino-n-propyl)-1,2-O-isopropylideneglucofuranose,

3-O-2'-(N',N'-dimethylaminopropyl)-1,2-O-isopropylideneglucofuranose,

6-O-3'-(N',N'-dimethylamino-n-propyl)-1,2-O-isopropylidenegalactopyranose,

6-O-2'-(N',N'-dimethylaminopropyl)-1,2-O-isopropylidenegalactopyranose,

3-O-3'-(N',N'-dimethylamino-n-propyl)-1,2:5,6-di-O-isopropylideneglucofuranose,

3-O-4'-(N'-methylpiperidyl)-1,2:5,6-di-O-isopropylideneglucofuranose,

3-O-2'-(N',N'-dimethylaminoethyl)-1,2:5,6-di-O-isopropylideneglucofuranose,

3-O-3'-(2',N',N'-trimethylamino-n-propyl)-1,2:5,6-di-O-isopropylideneglucofuranose, 3-O-2'-(N',N'-dimethylaminopropyl)-1,2:5,6-di-O-isopropylideneglucofuranose, 6-O-3'-(N',N'-dimethylamino-n-propyl-1,2:3,4-di-O-isopropylidenegalactopyranose, 6-O-2'-(N',N'-dimethylaminopropyl)-1,2:3,4-di-O-isopropylidenegalactopyranose, -N',N'-dimethylamino-iso-propyl-2,3:5,6-di-O-isopropylideneglucofuranoside, and organic and inorganic acid salts thereof.

Species of the foregoing novel compounds which possess striking wide spectrum antiviral activity are as follows:

3-O-3'-(N',N'-dimethylamino-n-propyl)-1,2-O-isopropylidene-D-glucofuranose,

3-O4'-(N'-methylpiperidyl)-1,2-O-isopropylidene-D-glucofuranose,

3-O-2'-(N',N'-dimethylaminoethyl)-1,2-O-isopropylidene-D-glucofuranose,

3-O-3'-(2',N',N'-trimethylamino-n-propyl)-1,2-O-isopropylidene-D-glucofuranose,

3-O-2'-(N',N'-dimethylaminopropyl)-1,2-O-isopropylidene-D-glucofuranose,

6-O-3'-(N',N'-dimethylamino-n-propyl)-1,2-O-isopropylidene-D-galactopyranose,

6-O-2'-(N',N'-dimethylaminopropyl)-1,2-O-isopropylidene-D-galactopyranose,

3-O-3'-(N',N'-dimethylamino-n-propyl)-1,2:5,6-di-O-isopropylidene-D-glucofuranose, 3-O-4'-(N'-methylpiperidyl)-1,2:5,6-di-O-isopropylidene-D-glucofuranose, 3O-3'-(2',N',N'-trimethylamino-n-propyl)-1,2:5,6-di-O-isopropylidene-D-glucofuranose, 3-O-2'-(N',N'-dimethylaminoethyl)-1,2:5,6-di-O-isopropylidene-D-glucofuranose, 3-O-2'-(N',N'-dimethylaminopropyl)-1,2:5,6-di-O-isopropylidene-D-glucofuranose, 6-O-3'-(N',N'-dimethylamino-n-propyl)-1,2:3,4-di-O-isopropylidene-D-galactopyranose, 6-O-2'-(N',N'-dimethylaminopropyl)1,2:3,4-di-O-isopropylidene-D-galactopyranose, α-N',N'-dimethylamino-iso-propyl-2,3:5,6-di-O-isopropylidene-D-glucofuranoside, and organic and inorganic acid salts thereof.

In general, the preparation of the monosubstituted compounds described herein involves the formation of alkyl ethers or substituted alkyl ethers at selected positions on the desired monosaccharide derivative, such as at position 3-O- of 1,2-O-isopropylidene-D-glucofuranose or 1,2:5,6-di-D-glucofuranose, position 6-O- of 1,2-O-isopropylidene-D-galactopyranose or 1,2:3,4-di-O-isopropylidene-D-galactopyranose, and position 3-O- of 1,2-O-isopropylidene-D-fructopyranose or 1,2:5,6-di-O-isopropylidene-D-fructopyranose. The condensation of the substituent substrate with the monosaccharide derivative at the desired position may be achieved by various prior art techniques. One method is described in U.S. Pat. No. 2,715,121, issued Aug. 9, 1955, to GLEN et al., the disclosure of which is incorporated herein by reference. The method described in this patent requires extreme reaction conditions and often gives low yields. The product purity is also less than satisfactory.

The preferred method of preparation involves much milder reaction conditions than employed in U.S. Pat. No. 2,715,121. The side reactions are minimized, the purity of the final product is greatly improved and the method may be adapted to a series of solvents having varying properties such as dioxane, tetrahydrofuran and benzene. Briefly, the improved method involves the reaction of a monosaccharide derivative which is blocked with one or more organo groups in the hydroxyl group positions adjacent the desired position to be substituted. The blocked monosaccharide is dissolved in one of the foregoing solvents and is reacted with a halogenated organo amino compound having the desired carbon chain length and configuration in the presence of a base such as sodium hydroxide. Selective removal of one or more blocking groups may be accomplished by hydrolysis under specific conditions resulting in a new product which is to be considered a compound of this invention. The reaction of either the block compound or the hydrolyzed compound with any organic or inorganic acid to form a salt thereof or with any organic or inorganic base to form a salt thereof results in a compound of this invention.

It is understood that simple derivatives of the compounds described herein are embraced by the invention. Such derivatives may be prepared by prior art techniques and procedures and used as an ingredient in the therapeutic composition and method of the invention.

For example, the free amine compounds are basic and form organic acid salts and inorganic acid salts, and the resulting salts are useful in the therapeutic composition and method of the invention. The salts may be prepared by the usual prior art techniques, such as by adding the free amine compound to water and then adding the desired organic acid or mineral acid thereto in an amount sufficient to neutralize the free amine. Examples of suitable acids include HCl, HBr, $H_2SO_4$, $HNO_3$, benzoic acid, p-aminobenzoic acid, p-acetamido-benzoic acid, p-hydroxybenzoic acid, alkane sulfonic acid, p-toluene sulfonic acid, acetic acid, alkylcarboxylic acids, oxalic acid, tartaric acid, lactic acid, pyruvic acid, malic acid, succinic acid, gluconic acid and glucuronic acid. The aqueous solution of the resulting salt is evaporated to the volume necessary to assure precipitation of the salt upon cooling. The precipitated salt is recovered by filtration, washed and dried to obtain a final amine salt product. The amine salts are often preferred for use in formulating the therapeutic compositions of the invention as they are crystalline and relatively nonhygroscopic. The amine salts are also better adapted for intramuscular injection than are the free amines.

Prior art blocking techniques may be employed such as acetonization and acetylation. Suitable prior art blocking methods are described in the aforementioned U.S. Pat. No. 2,715,121 and are described in the specific examples appearing hereinafter. In instances where an aldehyde or ketone is reacted with hydroxyl groups on adjacent carbon atoms, the initial compound may be dissolved in the desired aldehyde or ketone under anhydrous conditions and a Lewis acid catalyst is added in a catalytic quantity, such as 1% zinc chloride or anhydrous phosphoric acid. Often acetone is the preferred blocking agent, but aldehydes or ketones of much higher molecular weight may be used when desired such as those containing up to 25 carbon atoms. The reaction mixture is agitated at room temperature for a prolonged reaction period, such as 24–48 hours. The compound may be blocked in a plurality of positions, such as the 1,2- and 5,6- positions. It is usually preferred to block positions such as the 1,2- positions as the resulting partially blocked compound is much less toxic than compounds blocked in all available hydroxyl groups.

It is also possible to block one or more free hydroxyl positions of the compound with an ester group, wherein the carboxylic acid residue contains 1–18 and preferably 1–3 carbon atoms. The ester derivatives likewise may be prepared following prior art techniques such as by reacting a carboxylic acid anhydride with the compound following prior art practices. Additionally, the $\alpha$ or $\beta$ alkyl derivatives of monosaccharide derivatives such as 2,3:5,6-di-O-isopropylidene-D-glucofuranoside may be prepared following prior art techniques. In this latter instance, the compound is dissolved in a dry alcohol having the desired carbon chain length with aforementioned residua and reacted with the compound in the presence of a catalyst such as hydrogen chloride of Dowex 50 H+ resin. While the above discussed derivatives are presently preferred, it is understood that still other simple derivatives may be prepared following prior art techniques and then used in practicing the present invention. In addition to the foregoing, the compounds may also include monosubstitutions of monosaccharide derivatives in which the substrate

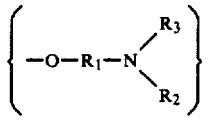

may be replaced by a substituent $R_7$, where $R_7$ is a deoxymonosaccharide derivative of halogen, keto, amino, lower alkyl, mercapto, alkenyl, alkynyl, aromatic, heterocyclic or alkylcarboxylic acid and its derivatives. $R_7$ may also represent the same groups as the above substrate of the monosaccharide derivative ethers. Still other antiviral agents have a general formula S—O—Y wherein Y is —$R_8$—S—$R_9$, where $R_8$ is a saturated or unsaturated hydrocarbon radical containing 1–7 carbon atoms and $R_9$ is a monovalent saturated or unsaturated hydrocarbon radical containing 1–7 carbon atoms and hydrogen.

The compounds of the invention are especially useful as wide spectrum antiviral agents for the therapeutic treatment of warm-blooded animals. They exhibit potent antiviral activity against both RNA and DNA viruses, contrary to the prior art antiviral agents. The compounds of the present invention exhibit marked suppression of virus particle multiplication and virus-induced cell injury in animal and human cell tissue culture systems against such widely varying viruses as herpes simplex, influenza A, mumps, poliovirus and rhinovirus. In tests in the whole animal, the compounds can reduce mortality and morbidity manifestations of influenza A infection by from 50 to 85%.

The compounds of the present invention may be administered to human patient or animal to be treated either orally or by parenteral administration. When the therapeutic composition is to be administered orally, the compound may be admixed with a prior art filler and/or binder such as starch and a disintegrator, and the admixture is pressed into a tablet of a size convenient for oral administration. Capsules also may be filled with the powdered therapeutic composition and administered orally. Alternatively, a water solution por suspension of the therapeutic composition may be admixed with a flavored syrup such as cherry syrup and administered orally. When the therapeutic composition is administered by intramuscular injection, the compound is usually dissolved in a physiological saline solution which contains sodium chloride in sufficient concentration to make the overall solution to be injected isotonic to body fluids. A salt of the free amine compound is usually preferred in instances where the compound is administered by intramuscular injection. In treating upper respiratory viral infections, the salt form in aqueous solution may also be administered by nasopharyngeal spary. Administration also may be by means of a suppository in patients unable to retain medication administered by mouth.

The dosage may be varied over extremely wide limits, as the compounds are effective at low dosage levels and are relatively free of toxicity and adverse side effects. The compounds may be administered in the minimum quantity which is therapeutically effective, and the dosage may be increased as desired up to the maximum dosage tolerated by the patient. Animal toxicity data indicate that the limiting nontoxic dosage may be up to 100–200 times the minimum effective dosage. Also, it is not necessary to carefully control the dosage for patients sensitive to the prior art antiviral drugs. As a general rule, the compound may be administered in an amount of about 1–40 milligrams per kilogram of body weight per day, and preferably in an amount of about 2–20 milligrams per kilogram per day, over the period required for treatment of the viral infection.

Surprisingly, the compounds described herein have still other unusual and unexpected therapeutically valuable properties. The learning of new tasks is enhanced. The therapeutic composition also protects against death due to water deprivation. The buffer capacity of the compounds over a pH range of approximately 7–9.8 is very good and they may be used for this purpose. Certain compounds also exhibit lubricative properties and may be used as a specialized lubricant. Compounds such as 3-O-D-glucopropionitrile and its derivatives are photosensitive and may be used in photographic applications.

It has been further discovered that the normal life span of tissue culture cells being grown in a prior art tissue culture medium may be extended very substantially and often by several fold by growing the cells in a tissue culture medium which contains an effective armount of one or more of the antiviral compounds described herein. This variant of the present invention is especially useful in the growing of human embryo cells and it has been observed that such cells survive for a significantly longer period of time in a tissue culture medium in the presence of as little as 2 micrograms per milliliter of one or more of the antiviral compounds described herein. However, much larger quantities of the compound may be present, such as the quantity described herein in the treatment of tissue culture cells infected with a virus, or in amounts up to the tolerance level of the cells. Preferably, the compound is 3-O-3'(N',N'-dimethylamino-n-propyl)-1:2-O-isopropylidene glucofuranose. This variant of the invention reduces research costs due to the longer life span of the tissue culture cells. It also has other positive effects as the surviving cells tend to be more vigorous and in a better state of preservation and more consistent research results are obtained.

[It has also been discovered that the antiviral compounds disclosed herein the pharmaceutical compositions containing the same, and the method of the invention are effective in the treatment of metastatic cancer in warm blooded animals. In practicing this variant of the invention, a warm blooded animals having a metastatic cancer, as carcinoma, is treated by administering thereto a therapeutically effective amount of at least one anti-viral compound disclosed herein. The compound may be administered at the dosage level described herein for common viral infections such as influenza. Often much larger quantities are more effective such as 10–50 times this amount, or quantities within the tolerance level of the warm blooded animal regardless of the amount. Death from cancer in warm blooded animals is caused by metastatic spread of the tumor cells, which in turn results from a greater freedom to translocate that individual cells develop when they become cancerous (Leighton, J., The Spread of Cancer. Academic Press, New York and London, 1967). The compounds used in the treatment of cancers specifically prevent this tendency to metastasis, thereby rendering the cancer non-malignant and allowing the warm blooded animal to live.]

The compounds used [in the treatment of metastatic cancer and/or] in the tissue culture medium in the growing of tissue culture cells are preferably the antiviral compounds disclosed herein. However, it is understood that the antiviral compounds disclosed in my earlier filed application Ser. No 337,134 also are useful for this purpose and may be substituted in equal quantities. The teachings of application Ser. No. 337,134 are therefore incorporated herein by reference.

The following specific examples further illustrate the present invention.

EXAMPLE 1

To a solution of 104 g (0.4 mole) of 1,2:5,6-di-O-isopropylidene-D-glucofuranose in 550 ml of 1,4-dioxane was added 189.7 g (1.2 mole) of 3-chloro-N,N-dimethylamino propane in the form of the hydrochloride salt and 144 g (3.6 mole) of sodium hydroxide. The suspension was mechanically stirred and heated to reflux for 18 hours. The reaction mixture thus prepared was filtered, the solids were washed with 1,4-dioxane and the washings were combined with the filtered liquid. The solvent was removed under reduced pressure and an amber-colored viscous oil was obtained.

The oil was distilled under high vacuum (less than 1 mm Hg) while using a very slight dry nitrogen purge to obtain high and low boiling fractions. The low boiling fraction was identified as unreacted 3-chloro-N,N-dimethylamino propane. The high boiling fraction had a boiling point of 148°–154° C at 2.5 mm Hg and was a clear viscous oil with an optical rotation of $\{\alpha\}_D^{25} = -19.3°$ neat (100 mm) and a density of 0.95 g/cc. The refractive index was $\eta_D^{21} = 1.4576$. Gas chromatography showed a purity greater than 99%. An elemental analysis showed: C, 59.13; H, 8.99; N, 4.12; O, 27.7. The yield was 80% of the novel compound 1,2:5,6-di-O-isopropylidene-3-O-3'-(N',N'-dimethylamino-n-propyl)-D-glucofuranose.

A portion of the above oil (10 g) was hydrolyzed in aqueous sulfuric acid at a pH value of 1.9–2.1 for 10 hours with refluxing. The resulting solution was adjusted to a pH value of 4.5 with saturated $Ba(OH)_2$ solution, centrifuged, and filtered through an ultrafine filter. The filtrate was lyophillized to a white-to-slightly yellow solid having a melting point of 78°–80° C. Gas chromatography data indicated above 99% purity of the novel compound 3-O-3'-(N',N'-dimethylamino-n-propyl)-D-glucopyranose. In thin-layer chromatography, the flow rate on silica gel with a solvent mixture composed of n-propanol, ethyl acetate, $H_2O$ and $NH_3$ in the ratio by volume of 60:10:30:10, respectively, was $R_f = 0.356$.

A portion of the oil is partially hydrolyzed to 1,2-O-isopropylidene-3-O-3'-(N',N'-dimethylamino-n-propyl)-D-glucofuranose by dissolving it in distilled water and adjusting the pH of the approximately 1M solution to 3.0±0.2 with 6N HCl. The solution is extracted twice with chloroform and the clear aqueous solution is refluxed for about two hours. Completion of partial hydrolysis reaction was monitored by gas chromatography from disappearance of the peak of parent compound and appearance of a new peak with larger retention time. The solution is then cooled, made alkaline with 30% sodium hydroxide to pH 10.5 and then extracted with chloroform. The chloroform phase is separated, dried over anhydrous magnesium sulfate and vacuum distilled to remove the solvent. The resulting colorless viscous oil has optical rotation of $\alpha_{neat}° = -12°$ and refractive index of 1.4687 at 25° C. Alternatively, the compound can be obtained as the hydrochloride salt by lyophilizing the aqueous solution after partial hydrolysis at pH 4.0–4.5. a white crystalline material is obtained which is recrystallized from methanol. The crystalline hydrochloride of 1,2-O-ispropylidene-3-O-3'-(N',N'-dimethylamino-n-propyl)-D-glucofuranose has a melting point of 181°–183° C and purity as indicated by gas chromatography is 98+%. Infrared spectrophotometry indicates the presence of strong —OH band which is not present in the parent oil. The elemental analysis for the hydrochloride salt in a typical batch showed: C, 49.09; H, 8.40; N, 4.14; Cl, 10.32; O, 28.12. Theoretical values are as follows: C, 49.19; H, 8.19; N, 4.09; Cl, 10.39; O, 28.11.

The gas-liquid chromatograms for the above intermediate and final novel compounds were run on a Beckman GC, Model 72-5 with a hydrogen flame detector. The column used for the intermediate novel compound was a commercially available SE-52 column, wherein methyl phenyl resins act as stationary phases supported on Chromosorb W (H.P.) which is made by Johns-Manville Corporation. The final novel compound was chromatographed on a Chromosorb 103 glass column, which is packed with porous resins. The foregoing materials are commercially available.

EXAMPLE 2

Starting with 51 g (0.3 mole) of 4-chloro-N-methylpiperidine hydrochloride and 26 g (0.1 mole) of 1,2:5,6-di-O-isopropylidene-D-glucofuranose and 36 g of NaOH in 150 ml 1,4-dioxane, condensation was accomplished using the general procedure outlined in Example 1. The residue remaining follow vacuum distillation was dissolved and recrystallized from hot methanol. The melting point was 106°–107.5° C (sharp).

Hydrolysis of the above product in $H_2SO_4$ at a pH value of 2.1 yielded 3-O-4'-(N'-methylpiperidyl)-D-glucopyranose having an optical rotation of $\{\alpha\}_D^{25} = +38.42°$ in $H_2O$. A gas chromatography analysis in accordance with Example 1 indicated that the purity of the product was in excess of 96%. The melting point was 62°–65° C.

EXAMPLE 3

A solution of 0.1 mole of 1,2:5,6-di-O-isopropylidene-D-glucofuranose in 50 ml of tetrahydrofuran was added to a suspension of 0.3 mole of 2-chloro-N,N-diethylaminoethane hydrochloride and 36 g of sodium hydroxide in 100 ml of tetrahydrofuran. The suspension was mechanically stirred and refluxed overnight and the reaction mixture was treated as set out in Example 1. The desired product, 1,2:5,6-di-O-isopropylidene-3-O-2'-(N',N'-diethylaminoethyl)-D-glucofuranose was obtained as a clear yellow liquid (boiling point 144°–150° C/0.15 mm Hg) having an optical rotation of $\{\alpha\}_D^{28} = -20.6°$ neat and a refractive index of $\eta_D^{25} = 1.4532$. The liquid solidified on exposure to air, probably due to formation of the carbonate salt. The yield was 85%.

Ten grams of the above product were hydrolyzed with aqueous sulfuric acid at pH value of 1.9–2.1 for ten hours under reflux. The resulting solution was adjusted to a pH value of 4–5 with saturated barium hydroxide solution and then centrifuged and filtered. Lyophilization of the filtrate yielded 6.55 g of light brown crystalline 3-O-2'-(N',N'-diethylaminoethyl)-D-glucopyranose. The optical rotation in water was $\{\alpha\}_D^{25} = +36.33°$. A gas chromatography analysis in accordance with Example 1 indicated that the purity was in excess of 99%.

EXAMPLE 4

To 26 g (0.1 mole) of 1,2:5,6-di-O-isopropylidene-D-glucofuranose and 36 g (0.9 mole) of sodium hydroxide in 150 ml of refluxing tetrahydrofuran was added dropwise over one hour 0.3 mole of 3-bromopropionitrile in 50 ml of tetrahydrofuran. The reaction mixture was refluxed for an additional six hours and then filtered. The solids were washed with tetrahydrofuran and the washings were combined with the filtrate. The solvent was removed under reduced pressure and solid 1,2:5,6-di-O-isopropylidene-3-O-3'-propionitrile-D-glucofuranose was obtained. The decomposition point was 165° C and it was light sensitive indicating utility in photographic applications.

Five grams (0.016 mole) of the above product was dissolved in anhydrous ether and added dropwise to a suspension of 0.76 g (0.02 mole) of lithium aluminum hydride in ether. The resulting complex was dissolved in cold hydrochloric acid and neutralized rapidly with sodium bicarbonate, The suspension thus produced was extracted with chloroform and the solvent was removed to obtain a yellow oil in a yield of 250 mg. Gas chromatography in accordance with Example 1 indicated a purity of 98% and there was a sharp infrared band at 3400 $cm^{-1}$. The oil was hydrolyzed at a pH value of 2.1 in sulfuric acid and lyophillized to dryness. The yield was 85 mg of 3-O-3'-(n-propylamino)-D-glucopyranose.

EXAMPLE 5

The 3-O-2'-(N',N'-dimethylaminopropyl) derivative of 1,2:5,6-di-O-isopropylidene-D-glucofuranose was prepared by condensing 0.1 mole of 1,2:5,6-di-O-isopropylidene-D-glucofuranose with 0.3 mole of 2-chloro-N,N-dimethylamino propane hydrochloride in the presence of 0.9 mole of sodium hydroxide in 150 ml of 1,4-dioxane. The reaction mixture was fractionally distilled under reduced pressure to obtain a yellow viscous oil (boiling point 142°-145° C/0.07 mm Hg) in 81% yield. The optical rotation was $\{\alpha\}_D^{25}=-21.5°$ neat and the refractive index was $\eta_D^{25}=1.4549$. Gas chromatography in accordance with Example 1 indicated only one component.

The above prepared yellow viscous oil (10 g) was hydrolyzed with aqueous sufuric acid at a pH value of 2.0 by refluxing for 10 hours. The pH value of the hydrolysate was adjusted to 4–5 with saturated barium hydroxide solution, filtered and lyophillized to obtain 10.5 g of light yellow crystals of 3-O-2'-(N',N'-dimethylaminopropyl)-D-glucopyranose. The optical rotation in water was $\{\alpha\}_D^{25}=+37.85°$. Gas chromatography in accordance with Example 1 indicated a purity in excess of 82%.

A portion of the oil, 1,2:5,6-di-O-isopropylidene-3-O-2'-(N',N'-dimethylaminopropyl)-D-glucofuranose, is partially hydrolyzed at pH 3.0±0.2 as indicated in Example 1. A white crystalline hydrochloride salt is obtained on lyophillization. The salt obtained is highly hygroscopic, with gas chromatographic purity being of the order of 80%.

EXAMPLE 6

To 0.1 mole of 1,2:5,6-di-O-isopropylidene-D-glucofuranose was added 0.3 mole of 2,N,N-trimethylaminopropyl chloride hydrochloride along with 36 g of sodium hydroxide. The general reaction procedure was in accordance with Example 1. The oil resulting from the reaction had a boiling point of 144°-146° C at 0.6 mm Hg and an optical rotation of $\{\alpha\}_D^{20}=-20.05°$ neat.

The above product was hydrolyzed according to the general method outlined in Example 1 to obtain the desired 3-O-3'-(2',N',N'-trimethylamino-n-propyl)-D-glucopyranose. The optical rotation of the product in water was $\{\alpha\}_D^{20}=+38.0°$.

A portion of the oil, 1,2:5,6-di-O-isopropylidene-3-O-3'-(2',N',N'-trimethylamino-n-propyl)-D-glucofuranose, is partially hydrolyzed at pH 3.0±0.2 according to the procedure mentioned in Example 1. A white crystalline 1,2-O-isopropylidene-3-O-3'-(2',N',N'-trimethylamino-n-propyl)-D-glucofuranose hydrochloride was obtained which is highly hygroscopic in nature. Optical rotation of the hydrochloride salt at pH 7.0 and 25° C is −21.33°. Gas chromatography analysis indicated better than 99% pure major component.

EXAMPLE 7

Using the general method outlined in Example 1, 0.02 mole of 1,2:5,6-di-O-isopropylidene-D-glucofuranose in 1,4-dioxane was reacted with 0.0225 mole of 2-(2-chloroethyl)-N-methylpyrrolidine hydrochloride and 0.0675 mole of sodium hydroxide. After 18 hours, the solvent was removed and the resulting orange oil was vacuum distilled under nitrogen. The residue consisted of the desired product, 1,2:5,6-di-O-isopropylidene-3-O-2'-{2''-(N''-methyl)-pyrrolidyl}-ethyl-D-glucofuranose having an optical rotation of $\{\alpha\}_D^{25}=-22.95°$ in chloroform.

EXAMPLE 8

1,2:5,6-di-O-isopropylidene-D-glucofuranose (0.1 mole) and N-(2-chloroethyl)-pyrrolidine hydrochloride (0.15 mole) are mechanically stirred and refluxed with 0.45 mole of sodium hydroxide in 150 ml of etrahydrofuran for 18 hours. The tetrahydrofuran is removed from the reaction products and the resulting oil is vacuum distilled under nitrogen. The 3-O-2'-}N'-pyrrolidyl)-ethyl}-1,2:5,6-di-O-isopropylidene-D-glucofuranose derivative has boiling point of 165°-171° C/0.15 mm Hg. Gas chromatography indicates a purity of 99%. Using the hydrolysis procedure outlined in Example 1, 10 g of the blocked oil was hydrolyzed and lyophillized giving a white hygroscopic crystalline solid.

EXAMPLE 9

The N',N'-dimethylamino-n-pentyl derivative of 1,2:5,6-di-O-isopropylidene-D-glucofuranose is made by condensing N,N-dimethylamino-n-pentyl-5-chloride hydrochloride with 1,2:5,6-di-O-isopropylidene-D-glucofuranose in the presence of pulverized sodium hydroxide in freshly purified, dry 1,4-dioxane as described in the procedure in Example 1. The product was confirmed by gas chromatography and infrared spectra.

N,N-dimethylamino-n-pentyl chloride hydrochloride is made from a commercially available sample of N,N-dimethylamino-n-pentyl alcohol by treatment with thionyl chloride ($SOCl_2$). Specifically, 10.7 g of thionyl chloride in a 250 ml three neck round bottom flask is cooled in a salt-ice water bath and stirred vigorously. To the cooled solution is added, dropwise, 10 g of N,N-dimethylamino-n-pentyl alcohol. The reaction is exothermic and the temperature is carefully controlled. The mixture is stirred for one hour after the evolution of $SO_2$ and HCl subsides. The mixture is brought to room temperature and allowed to stir overnight. Absolute alcohol is added to destroy excess thionyl chloride. Ten grams of crude N,N-dimethylamino-n-pentyl chloride hydrochloride is obtained as a white solid. This is used directly for the condensation reaction with 1,2:5,6-di-O-isopropylidene-D-glucofuranose without further purification. The alcohol and chloride can be resolved on a Chromosorb 103 gas chromatographyl column.

EXAMPLE 10

Bromine (9.8 g) was added slowly and dropwise to a mechanically stirred mixture of 50 g of cracked ice and a chilled aqueous sodium hydroxide solution (7 g/20 ml water). After the addition of bromine is complete, 15 g of 1,2:5,6-di-O-isopropylidene-3-O-acetamido-D-glucofuranose (prepared by the general procedure outlined in Example 1 by the condensation of 1,2:5,6-di-O-isopropylidene-D-glucofuranose with 2-chloroacetamide in the presence of sodium hydroxide) is added in four portions 15 minutes apart. The reaction mixture is heated for one hour in a water bath. After this time, an additional portion of the aqueous solution of sodium hydroxide (20 g/20 ml) is added and heating is continued for another hour. The mixture is cooled and extracted three times with ether. The ether extract is dried over anhydrous magnesium sulfate. The yellow hygroscopic solid remaining after evaporating off the ether is the desired 1,2:5,6-di-O-isopropylidene-3-O-aminomethyl-D-glucofuranose derivative. The product was identified by the disappearance of the carbonyl stretching at 1670 $cm^{-1}$ found in the parent acetamido compound.

EXAMPLE 11

Well established methodology of the prior art was employed to determine the antiviral potency of derivatives of 1,2-O-isopropylidene-D-glucofuranose HCl against poliovirus, type 1, and rhinovirus, type 1A, in tissue cultures at 37° C, employing HeLa cells with an agar overlay and WI-38 cells respectively. (See Wallis, C., F. Morales, J. Powell, and J. L. Melnick, Plaque enhancement of enteroviruses by magnesium chloride, cysteine, and pancreatin. J. Bacteriol. 91:1932–1935, 1966.) Poliovirus cell injury was determined by the study of plaque formation and rhinovirus was examined for cytopathic effect. In Table I, the virus inhibiting effects of three concentrations of the 3-O-3'-(N',N'-dimethylamino-n-propyl) derivative are depicted. The results are given as the degree of inhibition of infectivity, identified as plaque formation in the poliovirus system and as cytopathic effect in the system studying rhinovirus. The results indicate that, at the appropriate dose, the drug can completely inhibit 1000 plaque forming units (PFU) of poliovirus and a 1000 $TCID_{50}$ dose of rhinovirus 1A, which is a virus dose 1000 times that amount required to kill 50% of the tissue cultured cells.

TABLE I

DERIVATIVES OF 1,2-O—ISOPROPYLIDENE-D-GLUCOFURANOSE.HCl
SUMMARY OF ANTIVIRAL ACTIONS IN TISSUE CULTURE

| Derivative | Dose | System | Virus Type | Virus Titer | Determination | Drug Effect |
|---|---|---|---|---|---|---|
| 3-O—3'(N',N'—dimethylamino-n-propyl | 1 μg/ml | HeLa cells in vitro with agar overlay | Poliovirus type 1 | 50 PFU[1] | Plaque number | Total inhibition |
| " | 20 μg/ml | " | " | 250 PFU | " | " |
| " | 40 μg/ml | " | " | 1000 PFU | " | " |
| 3-O—3'-(N',N'—dimethylamino-n-propyl) | 2 μg/ml | WI-38 cells | Rhinovirus type 1A | 100 $TCID_{50}$[2] | Cytopathic effect | " |
| " | 20 μg/ml | " | " | 1000 $TCID_{50}$ | " | " |
| " | 40 μg/ml | " | " | 1000 $TCID_{50}$ | " | " |

[1]plaque-forming units.
[2]tissue culture infectious dose involving 50% of cells.

EXAMPLE 12

Derivatives of 1,2-O-isopropylidene-D-glucofuranose hydrochloride were examined for their capacity to suppress influenza $A_2$ disease in mice and for their capacity to suppress death and nonlethal nervous system disease produced by the encephalomyocarditis virus in mice. In these studies, drug effect on lung pathology produced by a 15 $ID_{50}$ dose of influenza virus was examined. This dose is 15 times the dose that produces disease in 50% of the animals. Disease and drug effect on disease were determined by lung weight increase and reduction thereof. In the encephalomyocarditis study, 10 times the dose capable of killing 50% of the animals was given, and the degree of nonlethal disease and death were determined, as well as drug inhibition of both of these parameters. The results for these experiments are summarized in Table II, and indicate the production of significant reduction in lung weight increased by drug, as well as a significant inhibition of death and nonlethal disease produced by encephalomyocarditis virus. These effects were more potent for the 3-O-3'-(N',N'-dimethylamino-n-propyl) derivative than for the other two derivatives studied.

TABLE II

DERIVATIVES OF 1,3-O—ISOPROPYLIDENE-D-GLUCOFURANOSE.HCl
SUMMARY OF ANTIVIRAL ACTIONS IN VIVO IN MICE

| Derivative | Dose | System | Virus Type | Virus Titer | Determination | Drug Effect |
|---|---|---|---|---|---|---|
| 3-O—3'-(N',N'—dimethylamino-n-propyl) | 20 mg/Kg | Mouse in vivo | Influenza type | 15 $ID_{50}$[1] | Lung weight increase | Significant reduction in lung weight increase |
| 3-O—3'-(N',N'—dimethylamino-n-propyl) | 80 mg/Kg | Mouse in vivo | Encephalomyocarditis | 10 $LD_{50}$[2] | Involvement of CNS[3] and death | Significant inhibition of death and nonlethal disease |
| " | 160 mg/Kg | " | " | " | " | " |
| 3-O—2'-(N',N'—dimethylamino-iso-propyl) | 80 mg/Kg | " | " | " | " | Inhibition significant, but less than n-propyl derivative |
| " | 160 mg/Kg | " | " | " | " | " |
| 3-O—3'-(2',N',N''—trimethyl-amino-n-propyl) | 80 mg/Kg | " | " | " | " | " |

TABLE II-continued

DERIVATIVES OF 1,3-O—ISOPROPYLIDENE-D-GLUCOFURANOSE.HCl
SUMMARY OF ANTIVIRAL ACTIONS IN VIVO IN MICE

| Derivative | Dose | System | Virus Type | Virus Titer | Determination | Drug Effect |
|---|---|---|---|---|---|---|
| " | 160 mg/Kg | " | " | " | " | " |

[1]infectious dose involving 50% of animals.
[2]lethal dose killing 50% of animals.
[3]central nervous system.

EXAMPLE 13

Human embryonic fibroblast cells, WI-38 type, were obtained from Microbiological Associates and grown in maintenance medium 199 with 1% fetal calf serum in the presence and absence of either 2, 20, or 40 μg/ml of 1,2-O-isopropylidene-3-O-3'-(N',N'-dimethylamino-n-propyl)-D-glucofuranose$^{HCl\ at}$ 37° C and 34° C. For cells grown at 37° C, survival of tissue cultured cells in the absence of drug diminished progressively through day 15, at which time 95% of cells failed to metabolize and no longer formed a monolayer. At 34° C, by 72 hours 95% of cells without drug were no longer actively metabolizing as determined by pH and a monolayer was no longer evident under microscopic examination. Addition of drug in the concentrations described above reduced this loss of viability by 75% at 15 days and 72 hours at 37° C and 34° C respectively.

[EXAMPLE 14]

[C57Bl/6J mice bearing transplanted melanoma B-16 were obtained from The Jackson Laboratories. This tumor was transplanted into recipient C57BL/6J mice at 10 days and the behavior of tumor growth in recipient mice was observed over two months. During this period, 90% of control animals died manifesting metastatic spread to the liver, bowel and kidney. Animals treated with 80 mg/Kg per day 1,2-O-isopropylidene-3-O-3''-(N',N'-dimethylamino-n-propyl)-D-glucofuranoseHCl, injected subcutaneously, exhibited significant central necrosis of primary tumors and only 15% succumbed to such cancer metastasis.]

I claim:

1. A [novel] therapeutic composition *for treating a warm blooded animal* comprising a pharmaceutically acceptable carrier containing [a therapeutically effective amount of] at least one [substance] *compound* selected from the group consisting of an [etheral] *ethereal* monosubstitution of a monosaccharide derivative having the formula S—O—Y, and therapeutically effective and pharmaceutically acceptable organic acid and inorganic salts thereof, wherein S is the residue of a [monosaccharide selected from the group consisting of pentoses, hexoses and heptoses] *hexose* which has been derivatized with at least one [substance] *compound* selected from the group consisting of (a) at least one aliphatic alcohol containing 1–18 carbon atoms to produce an [acetal] *ether* group at the site of at least one available hydroxyl group, (b) at least one aldehyde containing 1–18 carbon atoms to produce at least one acetal group at the site of at least one available hydroxyl group, (c) at least one ketone containing 1–18 carbon atoms to produce at least one ketal group at the site of at least one available hydroxyl group, and (d) at least one organic acid residue containing 1–18 carbon atoms to produce an ester group at the site of at least one available hydroxyl group, and Y is selected from the group consisting of [cyclic monovalent nitrogen containing organic] *piperidyl and pyrrolidyl* radicals and monovalent organic radicals having the formula

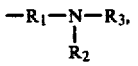

wherein $R_1$ is a divalent organic radical having a [linear crbon] *carbon* chain length of about [1–7] *1–4* carbon atoms and $R_2$ and $R_3$ are selected from the group consisting of [—H, —OH, —SH, halogen] *hydrogen* and monovalent organic radicals having a [linear] carbon chain length of about [1–7] *1–4* carbon atoms.

2. A [novel] therapeutic composition in accordance with claim 1 wherein Y is

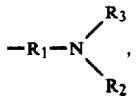

$R_1$ is a hydrocarbon radical having a [linear] carbon chain length of 1–3 carbon atoms, and $R_2$ and $R_3$ are selected from the group consisting of hydrogen and hydrocarbon radicals having a [linear] carbon chain length of 1–3 carbon atoms.

3. A [novel] therapeutic composition in accordance with claim 1 wherein Y is selected from the group consisting of -(n-propylamino),
-(N',N'-dimethylamino-n-propyl),
-(N',N'-dimethylaminoisopropyl),
-(N-methyl piperidyl),
-(N',N'-dimethylaminoethyl),
-(N',N'-dimethylaminoethyl), and
-(2',N',N'-trimethylamino-n-propyl).

4. A [novel] therapeutic composition in accordance with claim 1 wherein Y is -(N',N'-dimethylamino-n-propyl).

5. A [novel] therapeutic compostion in accordance with claim 1 wherein the said ethereal monosubstitution of the monosaccharide derivative has a formula selected from the group consisting of:

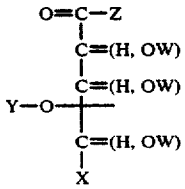

(a)

-continued (b)

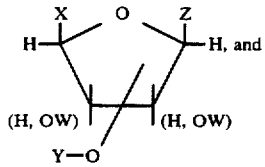

(c)

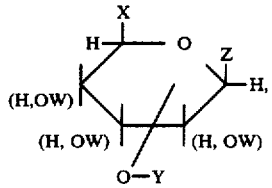

wherein X and Z are selected from the group consisting of H, OH, and monovalent hydroxyalkyl, alkoxyl and alkoxyalkyl radicals containing up to 3 carbon atoms, *said selection of X and Z being made to form a hexose,* W is selected from the group consisting of H and monovalent alkyl, alkenyl, cyclic alkane, cyclic aromatic, and acyl radicals containing 1–18 carbon atoms, Y represents the same organic radicals as set out in claim 1, and one of the OH groups, X or Z in said formula is replaced by —O—Y.

6. A [novel] therapeutic composition in accordance with claim 5 wherein Y is $$-R_1-\underset{\underset{R_2}{|}}{N}-R_3,$$

$R_1$ is a hydrocarbon radical having a [linear] carbon chain length of 1∝3 carbon atoms, and $R_2$ and $R_3$ are selected from the group consisting of hydrogen and hydrocarbon radicals having a [linear] carbon chain length of 1–3 carbon atoms.

7. A [novel] therapeutic composition in accordance with claim 5 wherein Y is selected from the group consisting of -(n-propylamino),
-(N',N'-dimethylamino-n-propyl),
-(N',N'-dimethylaminoisopropyl),
-(N-methyl piperidyl),
-(N',N'-dimethylaminoethyl),
-(N',N'-diethylaminoethyl), and
-(2',N',N'-triemthylamino-n-propyl).

8. A [novel] therapeutic composition in accordance with claim 5 wherein Y is -(N',N'-dimethylamino-n-propyl).

[9. A novel therapeutic composition in accordance with claim 5 wherein the monosaccharide is a hexose.]

[10. A novel therapeutic composition in accordance with claim 9 wherein Y is]

$$[\ -R_1-\underset{\underset{R_3}{|}}{N}-R_2\ ]$$

[$R_1$ is a hydrocarbon radical having a linear carbon chain length of 1–3 carbon atoms, and $R_2$ and $R_3$ are selected from the group consisting of hydrogen and hydrocarbon radicals having a linear carbon chain length of 1–3 carbon atoms.]

[11. A novel therapeutic composition in accordance with claim 9 wherein Y is selected from the group consisting of -(n-propylamino),
-(N',N'-dimethylamino-N-propyl),
-(N',N'-dimethylaminoisopropyl),
-(N-methyl piperidyl),
-(N',N'-dimethylaminoethyl),
-(N',N'-diethylaminoethyl), and
-(2',N',N'-triemthylamino-n-propyl).]

[12. A novel therapeutic composition in accordance with claim 9 wherein Y is -(N',N'-dimethylamino-n-propyl).]

13. A [novel] therapeutic composition in accordance with claim 5 wherein the monosaccharide is selected from the group consisting of glucose and galactose.

14. A [novel] therapeutic composition in accordance with claim 13 wherein the glucose is monosubstituted in the 1-O- or 3-O- position and the galactose is monosubstituted in the 6-O- position.

15. A [novel] therapeutic composition in accordance with claim 14 wherein Y is $$-R_1-\underset{\underset{R_2}{|}}{N}-R_3,$$

$R_1$ is a hydrocarbon radical having a [linear] carbon chain length of 1–3 carbon atoms, and $R_2$ and $R_3$ are selected from the group consisting of hydrogen and hydrocarbon radicals having a [linear] carbon chain length of 1–3 carbon atoms.

16. A [novel] therapeutic composition in accordance with claim 14 wherein Y is selected from the group consisting of -(n-propylamino),
-(N',N'-dimethylamino-n-propyl),
-(N'N'-dimethylaminoisopropyl),
-(N-methyl piperidyl),
-(N',N'-dimethylaminoethyl),
-(N',N'-diethylaminoethyl), and
-(2',N',N'-trimethylamino-n-propyl).

17. A [novel] therapeutic composition in accordance with claim 14 wherein Y is -(N',N'-dimethylamino-n-propyl).

18. A [novel] therapeutic composition in accordance with claim 13 wherein the ethereal monosubstitution of the monosaccharide derivative is selected from the group consisting of 3-O-3'-(N',N'-dimethylamino-n-propyl)-1, 2-O-isopropylidene-D-glucofuranose,
3-O-4-(N'-methylpiperidyl)-1,2-O-isopropylidene-D-glucofuranose,
3-O-2'-(N',N'-dimethylaminoethyl)-1, 2-O-isopropylidene-D-glucofuranose,
3-O-3'-(2',N',N'-trimethylamino-n-propyl)-1, 2-O-isopropylidene-D-glucofuranose,
3-O-2'-(N',N'-dimethylaminopropyl)-1,2-O-isopropylidene-D-glucofuranose,
6-O-3'-(N',N'-dimethylamino-n-propyl)-1, 2-O-isopropylidene-D-galactopyranose,
6-O-2'-(N',N'-dimethylaminopropyl)-1, 2-O-isopropylidene-D-galactopyranose,
3-O-3'-(N',N'-dimethylamino-n-propyl)-1, 2:5,6-di-O-isopropylidene-D-glucofuranose,
3-O-4'-(N'-methylpiperidyl)-1,2:5,6-di-O-isopropylidene-D-glucofuranose, 3-O-2'-(N',N'-dimethylaminoethyl)-1,2:5,6-di-O-isopropylidene-D-glucofuranose, 3-O-3'-(2',N',N'-trimethylamino-n-propyl)-1,2:5,6-di-O-isopropylidene-D-glucofuranose, 3-O-2'-(N',N'-dimethylaminopropyl)-1,2:5,6-di-O-isopropylidene-D-glucofuranose, 6-O-3'-(N',N'-dimethylamino-n-propyl)-1,2:3,4-di-O-isopropylidene-D-galactopyranose, 6-O-2'-(N',N'-dimethylaminopropyl)-1,2:3,4-di-O-isopropylidene-D-galactopyranose, -N',N'dimethylamino-iso-propyl-2,3:5,6-di-O-isopropylidene-D-glucofuranoside, and therapeutically effective and pharmaceutically acceptable organic and inorganic acid salts thereof.

19. A [novel] therapeutic composition in accordance with claim 13 wherein the ethereal monosubstitution of the monosaccharide derivative is 3-O-3'-(N',N'-dimethylamino-N-propyl)-1, 2-O-isopropylidene-D-glucofuranose.

20. A method of therapeutically treating *a viral infection in* a warm blooded animal comprising therapeutically administering thereto [a therapeutically effective amount of] at least one [substance] *compound* selected from the group consisting of an ethereal monosubstitution of a monosaccharide derivative having the formula S–O–Y, and therapeutically effective and pharmaceutically acceptable organic acid and inorganic acid salts thereof, wherein S is the residue of a [monosaccharide selected from the group consisting of pentoses, hexoses and heptoses] *hexose* which has been derivatized with at least one [substance] *compound* selected from the group consisting of (a) at least one aliphatic alcohol containing 1–18 carbon atoms to produce an [acetal] *ether* group at the site of at least one available hydroxyl group, (b) at least one aldehyde containing 1–18 carbon atoms to produce at least one acetal group at the site of at least one available hydroxyl group, (c) at least one ketone containing 1–18 carbon atoms to produce at least one ketal group at the site of at least one available hydroxyl group, and (d) at least one organic acid residue containing 1–18 carbon atoms to produce an ester group at the site of at least one available hydroxyl group, and Y is selected from the group consisting of [cyclic monovalent nitrogen containing organic] *piperidyl and pyrrolidyl* radicals and monovalent organic radicals having the formula

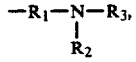

wherein $R_1$ is a divalent organic radical having a [linear] carbon chain length of about [1–7] *1–4* carbon atoms and $R_2$ and $R_3$ are selected from the group consisting of [—H, —OH, —SH, halogen] *hydrogen* and monovalent organic radicals having a [linear] carbon chain length of about [1–7] *1–4* carbon atoms, *said compound being administered in an amount which is therapeutically effective to treat such viral infection.*

21. The method of claim 20 wherein Y is

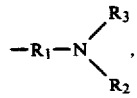

$R_1$ is a hydrocarbon radical having a [linear] carbon chain length of 1–3 carbon atoms, and $R_2$ and $R_3$ are selected from the group consisting of hydrogen and hydrocarbon radicals having a [linear] carbon chain length of 1–3 carbon atoms.

22. The method of claim 20 wherein Y is selected from the group consisting of -(n-propylamino), -(N',N'-dimethylamino-n-propyl), -(N',N'-dimethylaminoisopropyl), -(N-methyl piperidyl), -(N',N'-dimethylaminoethyl), -(N',N'-diethylaminoethyl), and -(2',N',N'-trimethylamino-n-propyl).

23. The method of claim 20 wherein Y is -(N',N'-dimethylamino-n-propyl).

24. The method of claim 20 wherein the said ethereal monosubstitution of the monosaccharide derivative has a formula selected from the group consisting of:

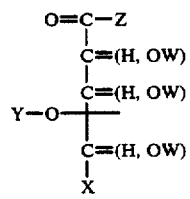

(a)

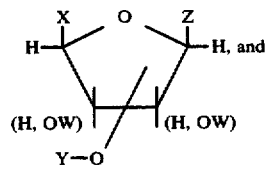

(b)

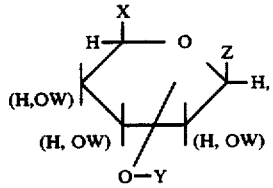

(c)

wherein X and Z are selected from the group consisting of H, OH, and monovalent hydroxyalkyl, alkoxyl and alkoxyalkyl radicals containing up to 3 carbon atoms, *said selection of X and Z being made to form a hexose,* W is selected from the group consisting of H and monovalent alkyl, alkenyl, cyclic alkane, cyclic aromatic, and acyl radicals containing 1–18 carbon atoms, Y [represents the same organic radicals and residua as set out in claim 1,] *is selected from the group consisting of piperidyl and pyrrolidyl radicals and monovalent organic radicals having the formula*

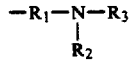

*wherein $R_1$ is a divalent organic radical having a carbon chain length of about 1–4 carbon atoms and $R_2$ and $R_3$ are selected from the group consisting of hydrogen and monovalent organic radicals having a carbon chain length of about 1–4 carbon atoms* and one of the OH groups, X or Z in said formula is replaced by —O—Y.

25. The method of claim 24 wherein Y is

[ $R_1-\underset{\underset{R_2}{|}}{N}-R_3$. ]

$R_1$ is a hydrocarbon radical having a [linear] carbon chain length of 1-3 carbon atoms, and $R_2$ and R are selected from the group consisting of hydrogen and hydrocarbon radicals having a [linear] carbon chain length of 1-3 carbon atoms.

26. The method of claim 24 wherein Y is selected from the group consisting of -(n-propylamino),
-(N',N'-dimethylamino-n-propyl),
-(N',N'-dimethylaminoisopropyl),
-(N-methyl piperidyl),
-(N',N'-dimethylaminoethyl),
-(N',N'-diethylaminoethyl), and
-(2',N',N'-trimethylamino-n-propyl).

27. The method of claim 24 wherein Y is -(N',N'-dimethylamino-n-propyl).

[28. The method of claim 24 wherein the monosaccharide is a hexose.]

[29. The method of claim 28 wherein Y is]

[ $-R_1-\underset{\underset{R_2}{|}}{N}-R_3$. ]

[$R_1$ is a hydrocarbon radical having a linear carbon chain length of 1-3 carbon atoms, and $R_2$ and $R_3$ are selected from the group consisting of hydrogen and hydrocarbon radicals having a linear carbon chain length of 1-3 carbon atoms.]

[30. The method of claim 28 wherein Y is selected from the group consisting of -(n-propylamino),
-(N',N'-dimethylamino-n-propyl),
-(N',N'-dimethylamino isopropyl),
-(N-methyl piperidyl),
-(N',N'-dimethylaminoethyl),
-(N',N'-diethylaminoethyl), and
-(2',N',N'trimethylamino-n-propyl).]

[31. The method of claim 28 wherein Y is -(N',N'-dimethylamino-n-propyl).]

32. The method of claim 24 wherein the monosaccharide is selected from the group consisting of glucose and galactose.

33. The method of claim 32 wherein the glucose is monosubstituted in the 1-O- or 3-O-position and the galactose is monosubstituted in the 6-O- position.

34. The method of claim 33 wherein Y is $-R_1-\underset{\underset{R_2}{|}}{N}-R_3$, $R_1$ is a hydrocarbon radical having a [linear] carbon chain length of 1-3 carbon atoms and $R_2$ and $R_3$ are selected from the group consisting of hydrogen and hydrocarbon radicals having a [linear] carbon chain length of 1-3 carbon atoms.

35. The method of claim 33 wherein Y is selected from the group consisting of -(n-propylamino),
-(N',N'-dimethylamino-n-propyl),
-(N',N'-dimethylaminoisopropyl),
-(N-methyl piperidyl),
-(N',N'-dimethylaminoethyl),
-(N,N'-diethylaminoethyl), and
-(2',N',N'-trimethylamino-n-propyl).

36. The method of claim 33 wherein Y is -(N',N'-dimethylamino-n-propyl).

37. The method of claim 32 wherein the ethereal monosubstitution of the monosaccharide derivative is selected from the group consisting of 3-O-3'-(N',N'-dimethylamino-n-propyl)-1, 2-O-isopropylidene-D-glucofuranose,
3-O-4-(N'-methylpiperidyl)-1,2-O-isopropylidene-D-glucofuranose,
3-O-2'-(N',N'-dimethylaminoethyl)-1,2-O-isopropylidene-D-glucofuranose,
3-O-3'-(2',N',N'-trimethylamino-n-propyl)-1, 2-O-isopropylidene-D-glucofuranose,
3-O-2'-(N',N'-dimethylaminopropyl)-1, 2-O-isopropylidene-D-glucofuranose,
6-O-3'-(N',N'-dimethylamino-n-propyl)-1, 2-O-isopropylidene-D-galactopyranose,
6-O-2'-(N',N'-dimethylaminopropyl-1, 2-O-isopropylidene-D-galactopyranose,
3-O-3'-(N',N'-dimethylamino-n-propyl)-1,2:5,6-di-O-isopropylidene-D-glucofuranose,
3-O-4'-(N'-methylpiperidyl)-1,2:5,6-di-O-isopropylidene-D-glucofuranose,
3-O-2'-(N',N'-dimethylaminoethyl)-1,2:5,6-di-O-isopropylidene-D-glucofuranose,
3-O-3'-(2',N',N'-trimethylamino-n-propyl)-1,2:5,6-di-O-isopropylidene-D-glucofuranose,
3-O-2'-(N',N'-dimethylaminopropyl)-1,2:5,6-di-O-isopropylidene-D-glucofuranose,
6-O-3'-(N',N'-dimethylamino-n-propyl)-1,2:3,4-di-O-isopropylidene-D-galactopyranose,
6-O-2'-(N',N'-dimethylaminopropyl)-1,2:3,4-di-O-isopropylidene-D-galactopyranose,
α-N',N'-dimethylamino-iso-propyl-2,3:5,6-di-O-isopropylidene-D-glucofurnaoside, and organic and inorganic acid salts thereof.

38. The method of claim 32 wherein the etereal monosubstitution of the monosaccharide derivative is 3-O-3'-(N',N'-dimethylamino-n-propyl)-1, 2-O-isopropylidene-D-glucofuranose.

39. In a method of growing tissue culture cells in a tissue culture medium in the absence of a viral infection wherein the tissue culture cells tend to die after being grown in the tissue culture medium over an extended period of time, the improvement which comprises increasing the life span of the tissue culture cells by growing them in a tissue culture medium which contains an effective amount of at least one [substance] *compound* selected from the group consisting of an ethereal monosubstitution of a monosaccharide derivative having the formula S—O—Y, and therapeutically effective and pharmaceutically acceptable organic acid and inorganic acid salts thereof, wherein S is the residue of [a monosaccharide selected from the group consisting of pentoses, hexoses] *hexose* [and heptoses] which has been derivatized with at least one [substance] *compound* selected from the group consisting of (a) at least one aliphatic alcohol containing 1-18 carbon atoms to produce an [acetal] *ether* group at the site of at least one available hydroxyl group (b) at least one aldehyde containing 1-18 carbon atoms to produce at least one acetal group at the site of at least one available hydroxyl group (c) at least one ketone containing 1-18 carbon atoms to produce at least one ketal group at the site of at least one available hydroxyl group, and (d) at least one organic acid residue containing 1-18 carbon atoms to produce an ester group at the site of at least one available hydroxyl group, and Y is selected from the group consisting of [cyclic monovalent nitrogen containing organic] *piperidyl and pyrrolidyl* radicals and monovalent organic radicals having the formula $$-R_1-\underset{\underset{R_2}{|}}{N}-R_3,$$

wherein $R_1$ is a divalent organic radical having a [linear]carbon chain length of about [1-7] *1-4* carbon atoms and $R_2$ and $R_3$ are selected from the group consisting of [—H, —OH, —SH, halogen] *hydrogen* and monovalent organic radicals having a [linear] carbon chain length of about [1-7] *1-4* carbon atoms.

40. The method of claim 39 wherein the ethereal monosubstitution of the monosaccharide derivative is 3-O-3'-(N',N'-dimethylamino-n-propyl)-1, 2-O-isopropylidene-D-glucofuranose.

41. The method of claim 39 wherein the tissue culture cells being grown in the tissue culture medium are human embryo cells.

42. The method of claim 41 wherein the ethereal monosubstitution of the monosaccharide derivative is 3-O-3'-(N',N'-dimethylamino-n-propyl)-1, 2-O-isopropylidene-D-glucofuranose.

[43. A method of therapeutically treating a metastatic cancer in a warm blooded animal comprising administering thereto a therapeutically effective amount of at least one substance selected from the group consisting of an ethereal monosubstitution of a monosaccharide derivative having the formula S—O—Y, and thereapeutically effective and pharmaceutically acceptable organic acid and inorganic acid salts, thereof, wherein S is the resiue of a monosaccharide selected from the group consisting of pentoses, hexoses and heptoses which has been derivatized with at least one substance selected from the group consisting of (a) at least one aliphatic alcohol containing 1-18 carbon atoms to produce an acetal group at the site of at least one available hydroxyl group, (b) at least one aldehyde containing 1-18 carbon atoms to produce at least one acetal group at the site of at least one available hydroxyl group, (c) at least one ketone containing 1-18 carbon atoms to produce at least one ketal group at the site of at least one available hydroxyl group, and (d) at least one organic acid residue containing 1-18 carbon atoms to produce an ester group at the site of at least one available hydroxyl group, and Y is selected from the group consisting of cyclic monovalent nitrogen containing organic radicals and monovalent organic radicals having the formula]

$$[\ -R_1-\underset{\underset{R_2}{|}}{N}-R_3.\ ]$$

[wherein $R_1$ is a divalent organic radical having a linear carbon chain length of about 1-7 carbon atoms and $R_2$ and $R_3$ are selected from the group consisting of —H, —OH, —SH, halogen and monovalent organic radicals having a linear carbon chain length of about 1-7 carbon atoms.]

[44. The method of claim 43 wherein the ethereal monosubstitution of the monosaccharide derivative is 3-O-3'-(N',N'-dimethylamino-n-propyl)-1, 2-O-isopropylidene-D-glucofuranose.]

45. A [novel] therapeutic composition in accordance with claim 1 wherein the said substance is in the form of a salt of an acid selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

46. The [novel] therapeutic composition in accordance with claim 45 wherein the said acid is HCl.

47. The [novel] therapeutic composition in accordance with claim 19 wherein the said 3-O-3'-(N',N'-dimethylamino-n-propyl)-D-glucose is in the form of a salt of an acid selected from the group consisting of HCl, HBr, $H_2SO_4$, $HNO_3$benzoic acid, p-aminobenzoic acid, p-acetamidobenzoic acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

48. The [novel] therapeutic composition in accordance with claim 47 wherein the said acid is HCl.

49. The method of claim 20 wherein the said substance is in the form of a salt of an acid selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

50. The method of claim 49 wherein the said acid is HCl.

51. The method of claim 38 wherein the said 3-O-3'-(N',N'-dimethylamino-n-propyl)-D-glucose is in the form of a salt of an acid selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

52. The method of claim 51 wherein the said acid is HCl.

*53. In a method of growing tissue culture cells in a tissue culture medium in the absence of a viral infection wherein the tissue culture cells tend to die after being grown in the tissue culture medium over an extended period of time, the improvement which comprises increasing the life span of the tissue culture cells by growing them in a tissue culture medium which contains an effective amount of at least one compound selected from the group consisting of ethereally monosubstituted monosaccharides having the formula S—O—Y, and therapeutically effective and pharmaceutically acceptable organic acid and inorganic acid salts thereof, wherein S is the residue of a hexose and Y is selected from the group consisting of piperidyl and pyrrolidyl radicals and monovalent organic radicals having the general formula*

$$-R_1-\underset{\underset{R_2}{|}}{N}-R_3,$$

*wherein $R_1$ is a divalent organic radical having a carbon chain length of about 1-4 carbon atoms and $R_2$ and $R_3$ are*

*selected from the group consisting of hydrogen and monovalent organic radicals having a carbon chain length of about 1–4 carbon atoms.*

*54. The composition of claim 1 wherein said monovalent nitrogen containing saturated, unsaturated or aromatic carbocyclic compounds contain about 5–6 carbon atoms in the ring; said branched or unbranched and saturated or unsaturated hydrocarbon radicals contain 1–3 carbon atoms; said carbocyclic acid residues contain 1–3 carbon atoms; and said aminohydrocarbon radicals contain 1–3 carbon atoms.*

*55. The method of claim 20 wherein said viral infection is an influenza, a mumps, or a herpes infection and wherein said compound is administered in an amount which is therapeutically effective to treat said influenza, mumps, or herpes infection.*

*56. The method of claim 21 wherein said viral infection is an influenza, a mumps, or a herpes infection and wherein said compound is administered in an amount which is therapeutically effective to treat said influenza, mumps, or herpes infection.*

*57. The method of claim 22 wherein said viral infection is an influenza, a mumps, or a herpes infection and wherein said compound is administered in an amount which is therapeutically effective to treat said influenza, mumps, or herpes infection.*

*58. The method of claim 32 wherein said viral infection is an influenza, a mumps, or a herpes infection and wherein said compound is administered in an amount which is therapeutically effective to treat said influenza, mumps, or herpes infection.*

*59. The method of claim 38 wherein said viral infection is an influenza, a mumps, or a herpes infection and wherein said compound is administered in an amount which is therapeutically effective to treat said influenza, mumps, or herpes infection.*

* * * * *

UNITED STATES PATENT AND TRADEMARK OFFICE

CERTIFICATE OF CORRECTION

PATENT NO. : RE. 33,000

DATED : July 25, 1989

INVENTOR(S) : Paul Gordon

It is certified that error appears in the above-identified patent and that said Letters Patent is hereby corrected as shown below:

Claim 6, column 21, line 37; "$\alpha$" should be -- - --.

Claim 25, column 25, line 1;

"$R_1$-N-$R_3$." should be -- $R_1$-N-$R_3$
$\quad\quad\;\; |\quad\quad\quad\quad\quad\quad\quad\quad |$
$\quad\quad\;\; R_2\quad\quad\quad\quad\quad\quad\quad\quad R_2$

Signed and Sealed this

Thirteenth Day of November, 1990

*Attest:*

HARRY F. MANBECK, JR.

*Attesting Officer*

*Commissioner of Patents and Trademarks*